United States Patent [19]

Goldberg et al.

[11] Patent Number: 4,544,027

[45] Date of Patent: Oct. 1, 1985

[54] SLUICE FOR COLLECTING CLEANING BODIES

[75] Inventors: Gerhard Goldberg, Düsseldorf; Alois Lange, Ratingen, both of Fed. Rep. of Germany

[73] Assignee: Taprogge Gesellschaft mbH, Düsseldorf, Fed. Rep. of Germany

[21] Appl. No.: 516,797

[22] Filed: Jul. 25, 1983

[30] Foreign Application Priority Data

Jul. 24, 1982 [DE] Fed. Rep. of Germany ....... 3227708

[51] Int. Cl.⁴ ............................................... F28G 1/00
[52] U.S. Cl. ....................................... 165/95; 15/3.51
[58] Field of Search ............ 165/95; 137/527.2, 527.6, 137/527.8; 15/3.51, 3; 122/379

[56] References Cited

U.S. PATENT DOCUMENTS

| | | | |
|---|---|---|---|
| 2,356,391 | 8/1944 | Fluor | 237/55 |
| 3,978,917 | 9/1976 | Honma et al. | 165/95 |
| 4,079,782 | 3/1978 | Soderberg et al. | 165/95 |

Primary Examiner—Henry Bennett
Attorney, Agent, or Firm—Herbert L. Lerner; Laurence A. Greenberg

[57] ABSTRACT

A sluice for collecting cleaning bodies in the form of sponge rubber balls which are guided in the circulation of cooling water through the pipes of a heat exchanger having inlet and outlet connections, in particular a generating plant condenser, includes a return line passing through the sluice, the return line including an inlet line having a pump and an outlet line having a shut-off valve, a cylindrical housing including a sieve body and a shutting flap connected downstream of the sieve body, the housing being connected to the outlet connection of the heat exchanger through the inlet line and being connected to the inlet connection of the heat exchanger through the outlet line, and a flap trap disposed in the return line for the cleaning bodies between the outlet connection and the inlet connection of the heat exchanger. In order to catch the sponge rubber balls in the sluice after switching off the pump, to prevent a backflow of cooling water and thus to prevent a discharge of the balls, a flap trap which is capable of shutting off the inlet line is positioned inside the sluice housing.

9 Claims, 7 Drawing Figures

SLUICE FOR COLLECTING CLEANING BODIES

This invention relates to a sluice for collecting cleaning bodies in the form of sponge rubber balls which are guided in the circulation of cooling water through the pipes of a heat exchanger, in particular a steam generating plant condenser, the sluice comprising a sieve body which is positioned in a cylindrical housing and has a shutting flap connected downstream, and is connected to the outlet connection of the heat exchanger via an inlet line provided with a pump, and is connected to the inlet connection of the heat exchanger via an outlet line provided with a shut-off valve.

Thus, according thereto, sponge rubber balls of this type are guided through the heat exchanger with the cooling water in circulatory operation, being removed from the flow of cooling water downstream of the heat exchanger and being re-supplied to the cooling water upstream of the heat exchanger. However, since the sponge rubber balls are generally not used continuously for cleaning purposes, but only at intervals, and since they must also be exchanged now and then, a suitable sluice is installed in the return line, as is known, for example from DE-OS 2,942,490.

A known arrangement of this type is shown schematically in FIG. 1. First of all, in this arrangement, the circulation of cooling water comprises a cooling water inlet connection 1, a heat exchanger 2 having an inlet chamber 3, heat exchanger pipes 4, a cooling water outlet chamber 5 and a cooling water outlet connection 6. A pivotal sieve 7 is positioned in the cooling water outlet connection 6, which sieve may be opened, in the event of possible soiling, as a function of a pressure control device, and thus may be rinsed. A sluice 10 is positioned parallel to the actual heat exchanger 2 between the cooling water outlet connection 6 and the cooling water inlet connection 1. This sluice 10 comprises a cylindrical housing 11, into which is inserted a funnel-shaped sieve 12. The sluice 10 is connected to the cooling water outlet connection 6 via an inlet line 13 which discharges into the upper region thereof. A motor-driven pump 14 and a motor-driven shut-off valve 15 are installed in this inlet line. The lower end of the sieve 12 is connected to a motor-driven shutting flap 17 via a tubular connection 16, and an outlet line 19 provided with a shut-off valve 18 discharges from the shutting flap 17 into the cooling water inlet connection 1.

During the circulatory operation of the sponge rubber balls, the valves 15 and 18 are opened, the shutting flap 17 is moved into the position shown in the Figure and the motor 14 is switched on. Consequently, the sponge rubber balls 20 which have been retained by the sieve 7 are conveyed into the sluice 10 via the inlet line 13 and since the shutting flap 17 produces a connection to the outlet line 19, the balls 20 are returned into the inlet connection 1 and from there are re-delivered into the cooling water.

If the sponge rubber balls 20 ae then to be caught and retained in the sluice 10, the shutting flap 17 must first of all be rotated by 90° so that the direct connection to the outlet line 19 is discontinued. Once all the sponge rubber balls 20 have been caught in the sieve 12, the pump 14 may then be turned off. However, due to the considerable difference in pressure between the cooling water inlet connection 1 and the cooling water outlet connection 6, there is then the danger that some of the flow of the cooling water will branch off and will flow back via the outlet line 19, the lower connection 21 of the shutting flap 17, the sieve and the inlet line 13 into the cooling water outlet connection 6 and, in so doing, will take the sponge rubber balls 20 with it. For this reason, it is necessary to close the shut-off valves 18 and 15, which is associated with a considerable expense because these valves are operated by hand for the most part.

Therefore, proceeding from this known arrangement and method of operation, an object of the present invention is to provide a sluice which is of a simpler design and is less susceptible to failure, and thereby allows a more reliable method of operation. This is of particular advantage if the cleaning installation is to be automated.

To achieve this object, the present invention provides the positioning of a flap trap in the return line, passing through the sluice, for the cleaning bodies, between the outlet connection and the inlet connection of the heat exchanger.

Such an arrangement of a flap trap ensures that when the pump is switched off, the cooling water is effectively prevented from flowing back through the sluice, without the two shut-off valves having to be closed. These valves only still have to shut off if, for example, the sponge rubber balls are to be removed from the sluice, are to be checked for damage and are optionally to be replaced by new sponge rubber balls.

The flap trap is appropriately positioned inside the sluice housing to block the inlet line. In this arrangement, it may be attached pivotally to the inside end of a tubular connection which is inserted into the opening of the inlet line. However, it is also possible for the flap trap to be attached pivotally in the region of the opening of the inlet line on the housing wall of the sluice itself.

The tubular connection may have at one end a rectangular flange, on the upper edge of which the flap trap which is also rectangular may be pivotally suspended in suitable holding loops.

To secure the tubular connection, it is advantageous for said connection to have slits which run in the longitudinal direction and for it to be clamped by means of said slits in an elastically resilient manner in the opening of the inlet line. However, it is also possible for the tubular connection to be bolted to the inlet line.

The closing movement of the flap trap may be effected by gravity alone or it may be assisted by spring force.

The construction and mode of operation of embodiments according to the present invention will now be described in more detail using further figures of a schematic drawing.

Figure 1:
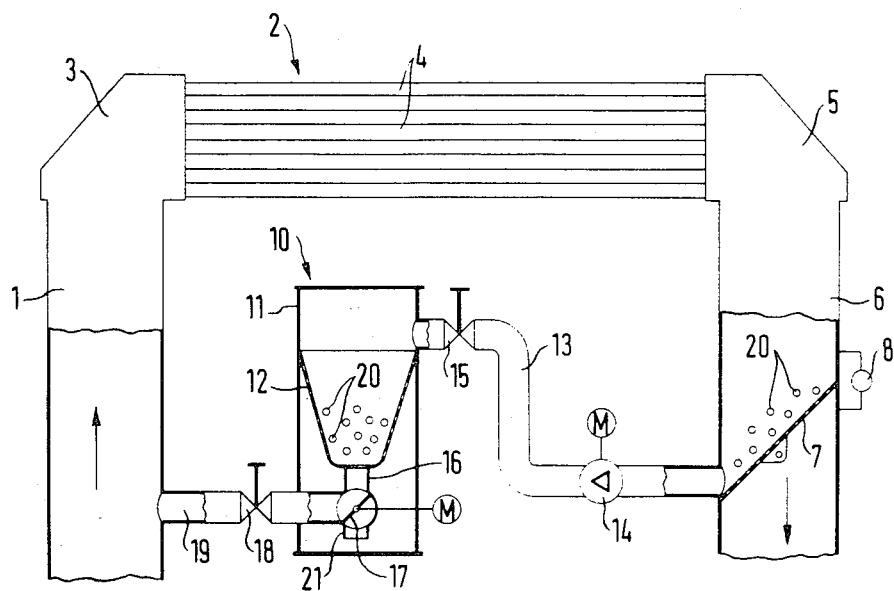
FIG. 1 shows a diagram of the known cleaning arrangement.
Figure 2:
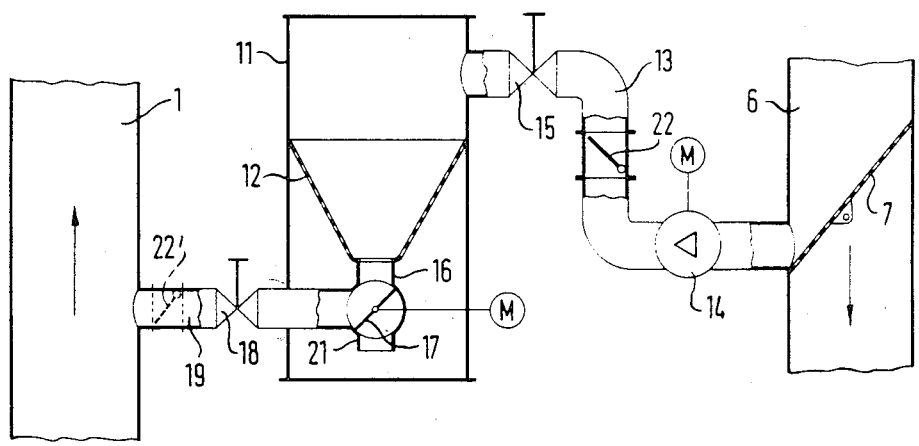
FIG. 2 shows a section of the complete arrangement with the basic position of the flap trap.

Proceeding from the known arrangement according to FIG. 1, in FIG. 2 according to the present invention, a flap trap 22 is positioned inside the inlet line 13 or the outlet line 19 which together form the return line for the cleaning bodies. The flap trap 22 may be installed in the inlet line 13, for example between the pump 14 and the shut-off valve 15. However, it is also possible to install a corresponding flap trap 22' in the outlet line 19, as shown in dashed lines.

In principle, it is possible to install the flap trap at any point between the outlet connection 6 of the heat exchanger 2 and the inlet connection 1 thereof, as a result of which it is possible to effectively prevent the cooling water, and thus the cleaning bodies 20, from flowing back when the pump 14 is switched off, and without the shut-off valves 15 and 18 having to be closed each time.

Figure 3:
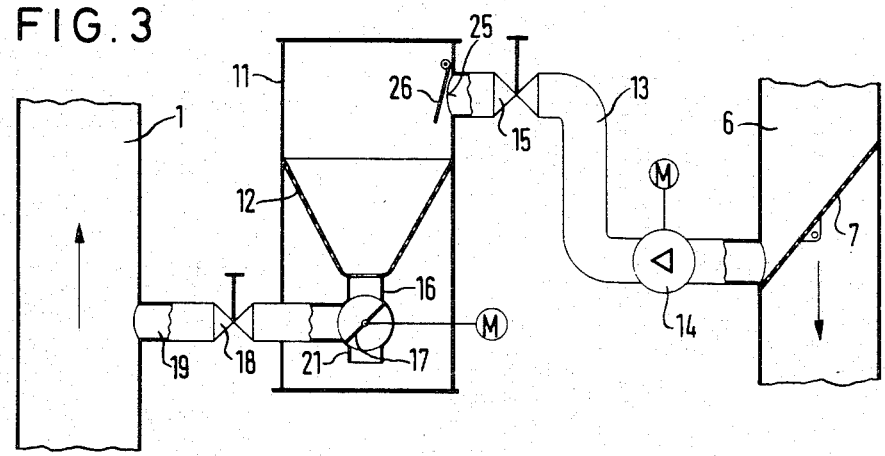
FIG. 3 shows the arrangement of the flap trap inside the sluice housing.
Figure 4:
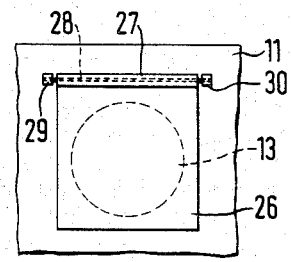
FIG. 4 shows the attachment of the flap trap directly to the housing wall.

FIG. 3 shows a particularly favorable arrangement of the flap trap - especially in terms of subsequent installation. According thereto, the flap trap 26 is positioned inside the sluice housing 11 at the opening 25 of the inlet line 13. As shown in the top view according to FIG. 4, this flap trap 26 may be directly attached to the inside wall 11 of the housing, in that a shaft 28 which penetrates a groove 27 in the upper edge of the rectangular flap trap 26 is held pivotally in two lateral hinges 29 and 30 which are attached to the housing wall 11. In this arrangement, the flap trap 26 may close by its force of gravity alone or it may be assisted in its closing action by a spring which is not shown in more detail. The flap trap 26 must merely close tightly enough so that sponge rubber balls 20 cannot be carried out of the sieve body 12 back into the inlet line 13. If necessary, the flap trap 26 may be designed in a slight curve corresponding to the radius of the cylindrical housing wall 11.

Figure 5A:
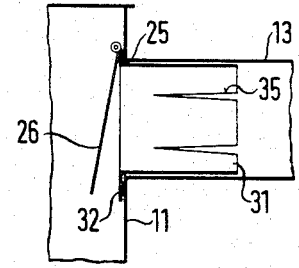
FIG. 5A shows a longitudinal section in the region of the inlet line having a flap trap attached to a tubular connection.
Figure 5B:
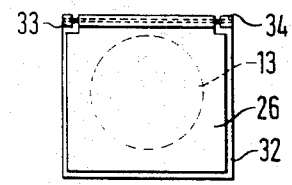
FIG. 5B shows a top view of the flap trap attached to the tubular connection.

FIGS. 5A and 5B show another appropriate type of attachment of the flap trap 26. According thereto, a tubular connection 31 is first of all inserted with an outwardly extending flange 32 on the inside end into the opening 25 of the inlet line 13 such that the flange 32 rests tightly against the housing wall 11 of the sluice 10. The flap trap 26 is then suspended pivotally in suitable hinges 33 and 34 on the upper edge on the inside flange 32 which appropriately has a rectangular outer contour of approximately the same size as the flap trap 26.

To improve the hold, the tubular connection 31 may have V-shaped slits 35 which run in the longitudinal direction and are open towards the inlet line 13, in which case, the tubular connection 13 is then clamped in an elastically resilient manner when inserted into the line 13, if the external diameter of the tubular connection 31 is the same as the internal diameter of the inlet line 13. In this way, an assembly is produced which, although very simple, ensures an adequate hold.

Of course, a different attachment of this tubular connection 31 is also possible, for example by means of bolts, but this method is not shown in more detail.

Figure 6:
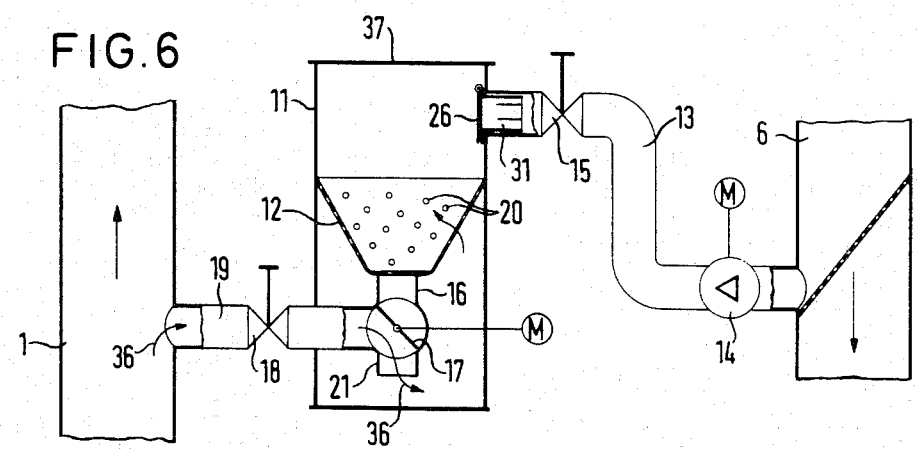
FIG. 6 is a diagram of the complete arrangement in the catching position of the sluice.

FIG. 6 shows the method of operation of the flap trap 26 in an essential phase of operation. In order to catch the sponge rubber balls 20 in the sieve 12, first of all the shutting flap 17 is rotated by 90° into the position shown in the Figure so that the direct passage for the sponge rubber balls from the sieve 20 to the outlet line 19 is discontinued. The pump 14 is then switched off. The by-pass flow which may build up as a result of the pressure difference between the cooling water inlet connection 1 and the cooling water outlet connection 6 will then pass back into the sieve 12 via the outlet line 19 and the lower connection 21 of the shutting flap 17, as shown by the arrows 36, but it will then impinge on the flap trap 26 which has closed in the meantime, as a result of which this by-pass flow 36 is stopped and thus sponge rubber balls 20 are prevented from being returned into the inlet line 13 and into the cooling water outlet connection 6 from the sieve body 12.

Thus, it is completely sufficient to change the position of the shutting flap 17 and to switch off the pump 14, which operations may be automated very easily, without other values having to be operated. Only if, for example the sluice 11 is to be opened by removing the upper cover 37 and if the sponge rubber balls 20 are to be removed, is it appropriate to also close the valves 18 and 15, which may be effected manually or using a servomotor.

In a normal case, the sponge rubber balls 20 are then redelivered to the cooling water circulation by switching on the pump 14 and moving the shutting flap 17 into the corresponding position to connect the sieve outlet connection 16 to the outlet line 19.

Therefore, with the arrangement which has been described and with the installation of a flap trap in the return line for the cleaning bodies, a solution is provided in a simple manner which is extremely reliable in operation and is practically trouble-free and which greatly reduces the hitherto necessary manipulation procedures of conventional cleaning body sluices.

We claim:

1. A sluice for collecting cleaning bodies in the form of sponge rubber balls which are guided in the circulation of cooling water through the pipes of a heat exchanger having inlet and outlet connections, in particular a generating plant condenser, comprising a return line passing through the sluice, the return line including an inlet line having a pump and an outlet line having a shut-off valve, a cylindrical housing including a sieve body and a shutting flap connected downstream of the sieve body, the housing being connected to the outlet connection of the heat exchanger through the inlet line and being connected to the inlet connection of the heat exchanger through the outlet line, and a flap trap disposed in the return line for the cleaning bodies inside the sluice housing between the outlet connection and the inlet connection of the heat exchanger to block the inlet line.

2. A sluice according to claim 1, wherein the flap trap is pivotally attached on the inside end of a tubular connection which is inserted into the opening of the inlet line.

3. A sluice according to claim 1, wherein the flap trap is pivotally attached to the housing wall in the region of the opening of the inlet line.

4. A sluice according to claim 2, wherein the tubular connection has at one end a rectangular flange, on the upper edge of which the flap trap which is also rectangular is pivotally suspended in suitable hinges.

5. A sluice according to claim 2, wherein the tubular connection has slits running in the longitudinal direction, and is clamped in an elastically resilient manner in the opening of the inlet line.

6. A sluice according to claim 2, wherein the tubular connection is bolted to the inlet line.

7. A sluice according to claim 2, wherein the closing movement of the flap trap is assisted by spring force.

8. A sluice according to claim 3, wherein the tubular connection has slits running in the longitudinal direction, and is clamped in an elastically resilient manner in the opening of the inlet line.

9. A sluice according to claim 3, wherein the closing movement of the flap trap is assisted by spring force.

* * * * *